United States Patent
Lasko et al.

(12) 
(10) Patent No.: US 6,277,104 B1
(45) Date of Patent: *Aug. 21, 2001

(54) AIR PERMEABLE, LIQUID IMPERMEABLE BARRIER STRUCTURES AND PRODUCTS MADE THEREFROM

(75) Inventors: Vincent Paul Lasko, New Egypt; Mary Gail Ciesielski, East Brunswick, both of NJ (US)

(73) Assignee: McNeil-PPC, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/917,987

(22) Filed: Aug. 25, 1997

(51) Int. Cl.[7] ................................................. A61F 13/15
(52) U.S. Cl. ................... 604/385.01; 604/368; 604/369; 604/370
(58) Field of Search ................ 264/41, 344; 604/367, 604/387, 385.01, 369, 370; 428/320.2

(56) References Cited

U.S. PATENT DOCUMENTS

| | | |
|---|---|---|
| 3,156,242 | 11/1964 | Crowe, Jr. . |
| 3,640,829 | 2/1972 | Elton . |
| 3,869,310 | 3/1975 | Fukushima et al. . |
| 3,870,593 | 3/1975 | Elton et al. . |
| 3,932,682 | 1/1976 | Loft et al. . |
| 3,953,566 | 4/1976 | Gore . |
| 3,962,153 | 6/1976 | Gore . |
| 3,989,867 | 11/1976 | Sisson . |
| 4,059,114 | 11/1977 | Richards . |
| 4,096,227 | 6/1978 | Gore . |
| 4,100,238 | 7/1978 | Shinomura . |
| 4,110,392 | 8/1978 | Yamazaki . |
| 4,178,271 | 12/1979 | Busch et al. . |
| 4,187,390 | 2/1980 | Gore . |
| 4,194,041 | 3/1980 | Gore et al. . |
| 4,197,148 | 4/1980 | Shinomura . |
| 4,197,371 | 4/1980 | Holst et al. . |
| 4,308,303 | 12/1981 | Mastroianni et al. . |
| 4,347,844 | 9/1982 | Ohki et al. . |
| 4,539,256 | 9/1985 | Shipman . |

(List continued on next page.)

FOREIGN PATENT DOCUMENTS

| | | | |
|---|---|---|---|
| 37 17 992 A1 | * | 12/1988 | (DE) . |
| 38 09 255 A1 | * | 9/1989 | (DE) . |
| 705583 | * | 4/1996 | (EP) ..................................... 604/387 |
| 2026381 | | 7/1979 | (GB) . |
| 2115702 | | 2/1983 | (GB) . |
| WO 90/14815 | * | 12/1990 | (WO) . |
| WO 91/03999 | * | 4/1991 | (WO) . |
| WO 91/09580 | * | 11/1991 | (WO) . |
| WO 91/09581 | * | 11/1991 | (WO) . |
| WO 93/01779 | * | 4/1993 | (WO) . |
| WO 95/10254 | * | 4/1995 | (WO) . |

*Primary Examiner*—Dennis Ruhl

(57) ABSTRACT

The present invention provides an air permeable, substantially liquid impermeable barrier structure and products made therefrom, such as sanitary napkins, pantiliners, incontinence products and diapers. The barrier structure has a porous layer having opposing sides, the porous layer having: a porous substrate having pores, which extend between the opposing sides that correspond to the opposing sides of the porous layer, whereby a liquid may transverse the substrate; and particles that are fused to at least one side of the porous substrate so as to restrict entry of the liquid into the pores; wherein the porous layer resists penetration by the liquid when it is contained in an absorbent structure that overlays the side of the porous layer to which the particles are fused, and is under a loading of one pound per square inch; and wherein the porous layer has a Frazier air permeability value in the range of greater than zero to about 80 mm$^3$/ft$^2$/min (861 mm$^3$/m$^2$/min).

22 Claims, 5 Drawing Sheets

U.S. PATENT DOCUMENTS

| | | |
|---|---|---|
| 4,560,611 | 12/1985 | Naka et al. . |
| 4,591,523 | 5/1986 | Thompson . |
| 4,609,584 | 9/1986 | Cutler et al. . |
| 4,622,036 | 11/1986 | Goodrum . |
| 4,648,876 | 3/1987 | Becker et al. . |
| 4,758,239 | 7/1988 | Yeo et al. . |
| 4,818,600 | 4/1989 | Braun et al. . |
| 5,441,056 * | 8/1995 | Weber et al. .................... 428/320.2 |
| 5,591,510 | 1/1997 | Junker et al. . |
| 5,695,871 * | 12/1997 | Tallentire et al. ............... 428/320.2 |
| 5,730,739 * | 3/1998 | Lavash et al. ...................... 604/387 |

* cited by examiner

AIR PERMEABLE, LIQUID IMPERMEABLE BARRIER STRUCTURES AND PRODUCTS MADE THEREFROM

FIELD OF THE INVENTION

This invention relates to sanitary protection products such as sanitary napkins, panty liners, incontinence products, diapers, surgical dressings and bedding underpads. In particular, this invention relates to air permeable, liquid impermeable barrier structures for such products.

BACKGROUND OF THE INVENTION

Sanitary protection products, such as sanitary napkins, panty liners, incontinence products, diapers and bedding underpads, are typically comprised of a body facing, liquid permeable cover, a garment facing, substantially liquid impermeable barrier sheet and an absorbent structure therebetween. The liquid impermeable barrier sheet is typically made of a thin, flexible plastic film that is impermeable to both liquids and vapors. The liquid permeable cover is also quite often made of a plastic film, similar to that of the barrier sheet, that is made perforate by creating two or three dimensional perforations in the film, thereby leaving plastic film land areas between the perforations. Such barrier sheets, as well as the land areas of the liquid permeable plastic film covers, do not permit vapors of liquids absorbed in the product to pass out from the product or permit liquids that collect on the surface of the user's body to enter into the product, the liquids being such as menstrual fluids, urine and perspiration. Such products typically feel uncomfortably hot when dry and clammy when wet.

Prior inventors have attempted to facilitate the transmission and removal of vapors from absorbent products by using inherently vapor transmitting liquid barrier materials or by creating, in liquid barrier materials, pores that are large enough to permit passage of vapors but not the passage of liquids. Such materials, and the products made therefrom, are commonly described as "breathable". Vapor permeable pores may be grouped into two categories, micropores and macropores, these being contained in microporous and macroporous materials respectively. Microporous materials are most resistant to liquid penetration and exhibit Frazier air permeability values of zero $mm^3/m^2/min$. However, they are also most resistant to vapor permeation, and therefore likely to be perceived by the user as not being breathable and not providing comfort and a dry feeling during wear. Macroporous materials, on the other hand, are most likely to be perceived as being breathable, exhibiting Frazier air permeability values that are greater than zero $mm^3/m^2/min$, thereby providing such comfort and dry feeling; but are also most likely to permit liquids to leak and therefore not provide protection against leakage from the absorbent product onto the user, the user's garment and beddothes.

Microporous Structures

Microporous structures are for the most part films with effective vapor transmitting micropore sizes that are equal to or greater than 100 Angstroms. Films may be inherently microporous, as for example those films made of polyurethanes. Such a film formed onto a base woven or nonwoven fabric is described in U.S. Pat. No. 4,560,611, where the coating solution consists of a polar organic solvent containing a polyurethane elastomer, a water repellent agent, e.g., a fluorine or silicone based material, a polyisocyanate and a nonionic surfactant. U.S. Pat. No. 4,197,371 discloses a sheet material of natural or synthetic rubber or a rubberlike polymer having uniformly incorporated particles of at least one swellable modified polymer such as modified starches and celluloses. U.S. Pat. No. 4,178,271 discloses a similar sheetlike material where the film is polyvinyl chloride or its copolymer. U.S. Pat. No. 3,869,310 discloses a leatherlike flexible sheet material, comprising a nonwoven fibrous mat and a polymeric impregnant, that has a porous structure and is not bonded to the fibers of the mat. The mat, composed of fibers prepared from at least two different polymeric materials, is first impregnated with a first liquid, that is a solvent for one of the polymeric materials and a nonsolvent for the other, to dissolve the soluble fibers; and then adding a second liquid, that is partially miscible with the first liquid and is a nonsolvent for all the polymeric fiber materials, to coagulate the resulting polymer solution.

Pores may be created in inherently nonporous films by means such as: stretching films in which thinned or stressed regions have been created or which noncompatible (to the film) inclusions have been incorporated. The stretching cause microfissures to form in the thinned or stressed regions or microseparations to form between the film and the noncompatible inclusions. Other means to create micropores comprise the incorporation in a film of soluble or volatile indusions that are removed by dissolving or volatilizing such inclusions. Still other means provide the blending into a polymer of fragmentable or abradable particles to form a sheet and then subjecting the sheet to a compressive force that breaks the particles to form micropores or to abrade the sheet to form micropores. UK Patent Application GB No 2,026,381 discloses the preparation of porous membranes by blending a polymer with a liquid component to form a binary two-phase system which in the liquid aggregate state has regions that are miscible and regions that have miscibility gaps. UK Patent Application GB No 2,115,702B discloses a liquid impermeable, vapor permeable backing that is composed of a film made by molding a mixture of a polyolefin resin and a liquid or waxlike hydrocarbon polymer into a film and then stretching the film laterally and/or longitudinally to more than 1.2 times its original dimension to create fine pores in the film. U.S. Pat. Nos. 3,953,566, 3,962,153, 4,096,227, 4,110,392, 4,187,390 and 4,194,041 disclose the preparation of porous sheets, and other porous articles, by extruding a paste comprised of particles of polytetrafluoroethylene, which is a nonthermoplastic polymer, and a lubricant, and then removing the lubricant and stretching and annealing the resultant product. The resulting product is a sintered, oriented porous film characterized by having polymer nodes connected by fibrils. Somewhat related to these patents, and yielding a soft dothlike liquid permeable sheet material, is U.S. Pat. No. 4,622,036 which discloses such a sheet material consisting of particles of nondissolvable polyolefin or polyvinyl chloride that are partially fused together by heat so as to provide a desired amount of liquid permeability, the particles ranging in size from about one to 2000 microns, and the sheet having a thickness from about 0.0005 to 250 inches.

U.S. Pat. Nos. 4,100,238 and 4,197,148 describe the preparation of microporous films by extruding a two component blend from which one component is leached out with a solvent, and then stretching the leached film to obtain a desired porosity in a soft dothlike liquid permeable sheet material. U.S. Pat. Nos. 3,214,501, 3,640,829 and 3,870,593 disclose the preparation of a microporous polymer sheet by blending into a polymer nonmiscible, nonleachable fillers such as starch and salts, forming the sheet and then stretching the sheet to form pores that are initiated at the sites of the filler particles. U.S. Pat. No. 4,347,844 discloses the preparation of a porous sheet, for use in a disposable diaper, by blending a particulate substance into a polymer, forming a sheet and then breaking the particulate substance within the sheet under a compressive force to create micropores. U.S. Pat. No. 4,308,303 discloses a flocked foam coated fiber reinforced water vapor permeable barrier, having a fabric appearance and capable of filtering bacteria, comprising a microporous polyolefin film coated on at least one surface with a foamed latex polymer, flocked fibers on the outside of the foamed latex polymer and a web of spunbonded fibers on the outside of the flocked foamed latex polymer. The film is rendered microporous by stretching. The film becomes microporous because it has minute fracture sites or pore nucleating agents such as finely divided filler, preferably calcium carbonate, of particle size less than 3 microns, and/or minute crystalline domains. U.S. Pat. No. 4,609,584 discloses the preparation of a porous sheet, for use in a disposable diaper, by blending a particulate substance into a polymer, forming a sheet and then abrading or buffing the surface of the sheet to create micropores. U.S. Pat. Nos. 4,539,256 and 4,609,584 disclose methods for making microporous sheets that comprise the steps of melt blending a crystallizable thermoplastic polymer with a compound that is miscible with the polymer at the polymer's melting temperature, but not below that temperature, forming a sheet of the melt blend, and then cooling the sheet to a temperature at which the compound becomes immiscible with the polymer and phase separates. When the sheet is oriented at least in one direction, a network of interconnected micropores forms between the polymer phase and the compound phase. The compound may be removed from the sheet by solvent extraction.

U.S. Pat. No. 3,156,242 discloses a flexible absorbent sheet, of for example polyethylene, that is useful as a backing sheet or as an outer layer of a surgical dressing, the sheet being microporous. However, the sheet may have holes or slits formed in it, to make it macroporous. U.S. Pat. No. 3,426,242 discloses a breathable medical dressing having a backing comprised of an open celled structure, i.e., a film processed to have voids with passageways to its outside surfaces that are generally less than 5000 Angstroms, e.g., from 100 to 5000 Angstroms, the film having a final crystallinity of at least 40%. The film is preferably coated with a continuous layer of microporous pressure sensitive adhesive. U.S. Pat. No. 3,932,682 describes waterproof products, capable of transmitting air and water vapor, that are made by spray spinning filamentary material, e.g., by meltblowing, onto an open celled polymer film to obtain thermal self-bonding or by spraying the filamentary material onto an elastic film, then stretching the resulting product to yield an open celled structure and heat setting the stretched product to impart dimensional stability. U.S. Pat. Nos. 4,758,239 and 4,818,600 disclose a breathable barrier that includes a fibrous porous sheet, preferably a meltblown web, to which is joined a nonmicroporous film, wherein some of the fibers at the joined surface are intimately commingled with the film to give a vapor transmission rate at 37° C. and 50% RH of about 100–5000 g/m$^2$/24 hrs and is impermeable to 0.9% saline for at least one hour at 21° C. for about one hour at a hydrostatic head of at least 11.4 cm. The film may be a preformed film of a water soluble polymer such as polyvinyl alcohol.

Macroporous Structures

U.S. Pat. No. 3,989,867 discloses an absorptive device having a backsheet with bosses and uniformly small apertures at the apices of the bosses. The apertures take up from 0.5 to 10% of the available permeation area of the backsheet to allow vapor transmission while preventing liquid passage at pressures typically encountered in use. U.S. Pat. No. 4,591,523 describes an apertured, macroscopically expanded, three dimensional polymeric web useful as a breathable, fluid resistant barrier for a disposable diaper. The web preferably comprises a deeply drawn three dimensional structure containing a multiplicity of debossments of macroscopic cross section. Each debossment originates as an aperture in a first surface of the web, has continuous sidewalls that terminate to form an end wall in a second parallel surface of the web, the end wall including multiple apertures that are sized and shaped to support an aqueous fluid meniscus and being spaced one from another so that the fluid menisci do not contact each other. U.S. Pat. No. 4,059,114 describes a disposable shield for garment protection and every day feminine hygiene that has a fluid barrier in the form of a soft, rattle free moisture permeable layer that is preferably a liquid impermeable layer of a blown microfiber web. U.S. Pat. No. 5,591,510 discloses a layered fabric material that is breathable and resists fluid penetration which comprises a breathable and fluid penetration resistant nonwoven and a plastic film that has perforations that are disposed from about 5° to 60° to the film's surface.

It is an objective of this invention to provide perceptibly breathable vapor permeable, macroporous barrier structures, and sanitary protection products made therefrom, that restrict the passage of liquids under use conditions, and therefore give protection against liquid leakage as well as user-perceptible comfort and dry feeling.

SUMMARY OF THE INVENTION

The present invention provides an air permeable, substantially liquid impermeable barrier structure that has a porous layer having opposing sides, the porous layer having: a substrate having pores, which extend between the opposing sides that correspond to the opposing sides of the porous layer, whereby a liquid may transverse the substrate; and particles that are fused by being sintered to at least one side of the porous substrate so as to restrict entry of the liquid into the pores; wherein the porous layer resists penetration by the liquid when it is contained in an absorbent structure that overlays the side of the porous layer to which the particles are fused, and is under a loading of one pound per square inch (70.3 g/cm$^2$); and wherein the porous layer has a Frazier air permeability value in the range of greater than zero to about 80 mm$^3$/ft$^2$/min (861 mm$^3$/m$^2$/min).

The air permeable, substantially liquid impermeable barrier structure is characterized by having the particles that are fused to the porous substrate being predominantly on the surface of the porous substrate rather than being admixed with and penetrating the depth of the materials that comprise the porous substrate.

The present invention also provides an absorbent product, such as a sanitary napkin, incontinence product, diaper, surgical dressing and bedding underpad, the absorbent product comprising a body facing liquid permeable sheet, an undergarment facing air permeable, substantially liquid impermeable barrier, and an absorbent structure therebetween; the barrier comprising the porous layer described above. The present invention additionally provides such absorbent products wherein the liquid permeable sheet has liquid permeable pores and substantially liquid impermeable, but air permeable regions, where such regions comprise the porous layer described above.

DETAILED DESCRIPTION OF THE INVENTION

Figure 1:
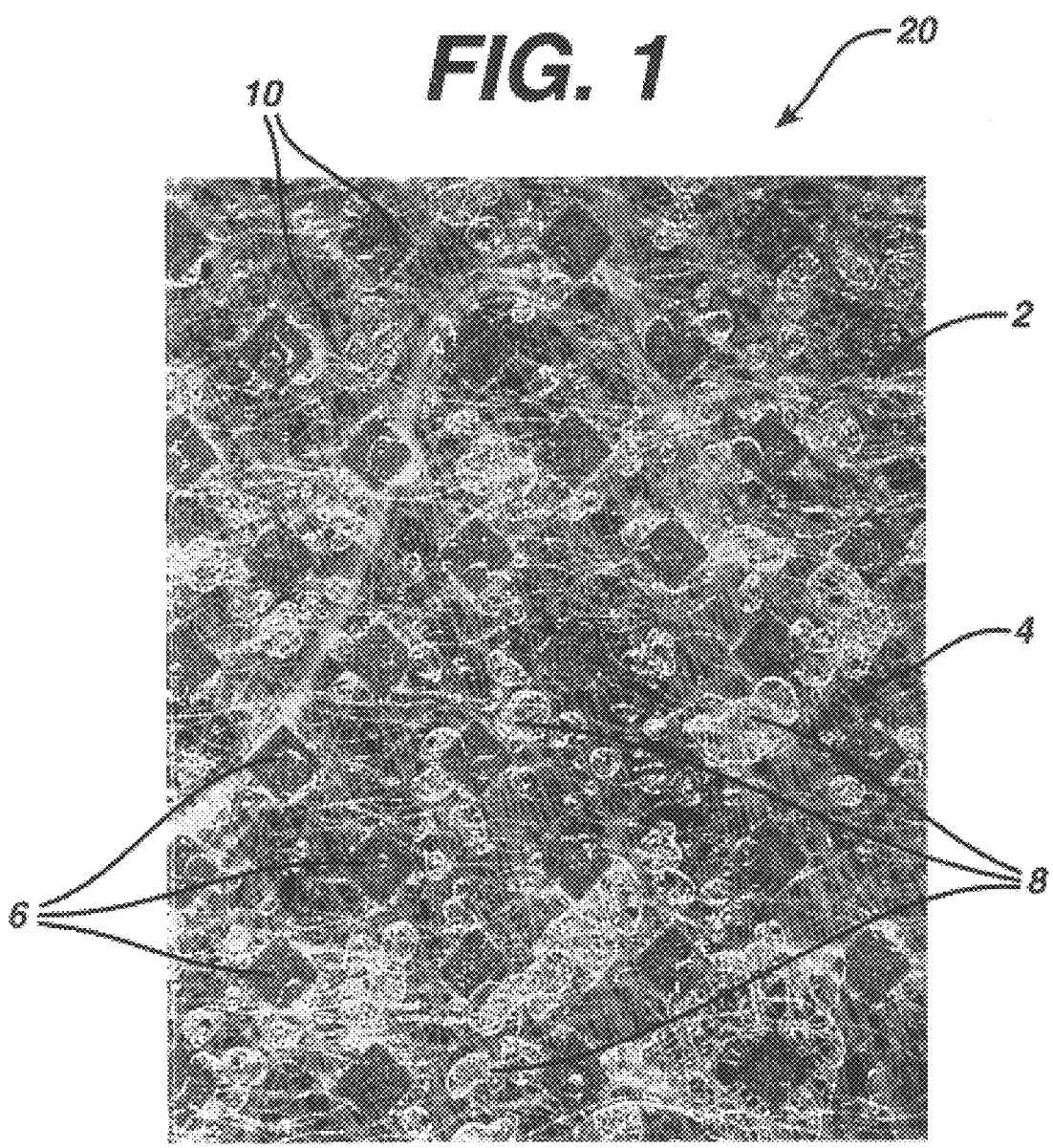
FIG. 1 is a plan view microphotograph of the air permeable, substantially liquid impermeable barrier structure of this invention.

The breathable, air permeable, substantially liquid impermeable barrier structures of this invention are macroscopically porous, in that they contain large pores some of which may be visibly large enough to be seen unaidedly, or with low magnification, e.g., about 5X. However, the size of the pores, and the materials used to restrict entry of liquid into the pores, as well as the method of attachment and position of attachment of the materials to the porous substrate, are such as to prevent liquid from passing through the barrier structures while unrestrictedly permitting gases and vapors to pass through. The air permeability of the barrier structures of this invention are distinguished from that of microporous structures in that it is greater than zero when measured by a method using a Frazier Air Permeometer, an instrument used to determine the air permeability of nonocclusive materials, such method being described below in the description of this invention. Being macroporous, the barrier structures of this invention are considered substantially impermeable to liquids, as part of absorbent products given above as examples, and under the conditions of use for such products. Thus the barrier structures of this invention are neither absolutely fluid impervious or limitedly impervious, to the degree that the barrier structures are microporous materials, the degree of permeability of such structures being measured by their bubble point. The resistance to leakage under use is measured under simulated conditions of use, the method of measurement being described further along in the description of this invention.

The barrier structures may form all of a component of an absorbent product, for example as the garment facing barrier of an absorbent product; or it may form part of a component of an absorbent product, for example as the land areas of a body facing, fluid permeable cover sheet. The barrier structures of this invention have a porous layer having opposing sides, the porous layer having: a porous substrate having pores, which extend between opposing sides that correspond to the opposing sides of the porous layer, whereby a liquid may transverse the substrate; and particles that are fused to at least one side of the porous substrate so as to restrict entry of the liquid into the pores; wherein the porous layer resists penetration by the liquid when it is contained in an absorbent structure that overlays the side of the porous layer to which the particles are fused, and is under a loading of one pound per square inch; and wherein the porous layer has a Frazier air permeability value that is in the range of greater than zero to about 80 $mm^3/ft^2/min$ (861 $mm^3/m^2/min$), preferably in the range of from about 5 $mm^3/ft^2/min$ (53.8 $mm^3/m^2/min$) to about 70 $mm^3/ft^2/min$ (753 $mm^3/m^2/min$), and most preferably in the range of from about 25 $mm^3/ft^2/min$ (269 $mm^3/m^2/min$) to about 60 $mm^3/ft^2/min$ (646 $mm^3/m^2/min$).

The porous substrate may be comprised of at least one of a nonwoven fabric, a woven fabric, a perforated film or a nonreticulated foam. The porous substrate may be fusible.

The nonwoven fabric typically has a basis weight of at least 8 grams per square meter. The nonwoven fabric may be comprised of at least one of thermoplastic staple fibers, thermoplastic filaments, nonthermoplastic staple fibers or nonthermoplastic filaments. The thermoplastic staple fibers and thermoplastic filaments may consist of such as polyethylene, polypropylene, polyester, polyamide, polacrylonitrile, bicomponent fibers and combinations thereof. The bicomponent fibers may be comprised of at least one of such as a polypropylene core with a polyethylene sheath, a polyester core with a polyethylene sheath, a polyester core with a polypropylene sheath, a polyester core with a lower melting polyester sheath, or combinations thereof. The nonthermoplastic fibers may be selected from such as cotton, rayon, woodpulp and combinations thereof.

The nonwoven may be comprised of fibers and filaments that are bonded to each other by bonding means comprised of at least one of thermal calender bonding, fusible powder bonding, adhesive binder bonding, spunbonding, meltblowing followed by calender bonding or hydroentangling.

The perforated films may have two or three dimensional perforations, the three dimensional perforations having sidewalls, the sidewalls being substantially either parallel or they may be aparallel to each other, as for example in perforations with tapered sidewalls. The perforations may be at the base of the sidewalls or in the sidewalls themselves. The perforations in the films may be made by methods such as puncturing by mechanical means such as punching or needling, by ultrasonic perforation, by hot air being drawn through the film supported on a porous substrate such as a screen or perforate drum, by water jet perforation and by thinning the film in discrete areas as by embossing followed by stretching to cause the thinned areas to burst. The films may have a smooth, matte, rough or embossed surface the embosses being either visible to the naked eye or requiring magnification for their visualization. The films may be made of any of several polymeric materials that are thermoplastically formed such as by extrusion, melt casting or solution casting, the materials being such as polyolefins such as polyethylene, polypropylene and polybutylene, polyesters, polyurethanes, polyamides, polyvinyl chloride, polyvinylidene chloride, ethyl acetate, copolymers of ethylenevinyl acetate, ethylene acrylic add, ethylene methacrylate, ethylene n-butylacrylate, and styrene copolymers with ethylene, propylene, butadiene, butylene and isoprene. The foam may be made from such as polyester polyurethanes, polyether polyurethanes and polyethylene.

Particles are fused to at least one side of the porous substrate so as to restrict entry of the liquid into the pores. This is done for example by adding the particles to the porous substrate so that essentially even, and uniformly spaced coverage of the substrate is achieved, either over the complete porous substrate or in discrete zones of the porous substrate, by means that are known to those skilled in the art such as feed augers, funnels and air entrainment of the particles. The particle covered substrate is transported to a heating means to fuse the particles to the substrate, the heating means being such as hot air or infrared heat. The substrate, now having fused particles adhered to it, is then preferably brought through a nip comprised of at least one chill roll so that the particles are flattened to increase the surface that will encounter fluid in use and so that the particles are well adhered to the surface of the substrate. At least one, of the porous substrate and the particles, must be fusible. However, the particles may be adhered to the substrate without fusing by the use of adhesive. It is preferred, in order to maintain the dimensional structure of the barrier structure, that the particles be fused onto the porous substrate at a temperature that is not greater than the melting point of the porous substrate. The resulting structure of the air permeable, substantially liquid impermeable barrier structure is distinguished by having the particles that are fused to the porous substrate, being predominantly on the surface of the porous substrate rather than being admixed with and penetrating the depth of the materials that comprise the porous substrate; and wherein the substantially liquid impermeable barrier structure is resistant to the passage of liquids under conditions of use such as the wearing of a sanitary napkin during menstruation.

It is preferred, for adequate coverage and resistance to fluid penetration that the particles be added-on to the substrate in an amount of at least about 9 grams per square meter, and more preferably in an amount of from between 9 and 36 grams per square meter ($g/m^2$).

The particles may be comprised of at least one of powder particles or fibers. Powder particles may be selected from the group consisting of polyethylene, polypropylene, polyester, ethylenevinyl acetate, ethylene acrylic acid, ethylene methacrylate, ethylene n-butylacrylate, polyester polyurethanes, polyether polyurethanes, styrene-isoprene-styrene copolymers, styrene-butadiene-styrene copolymers, styrene-ethylene-butylene-styrene copolymers, styrene-ethylene-propylene-styrene copolymers and combinations thereof. Fiber partides may be selected from the group consisting of polyethylene, polypropylene, polyester, polyamide, polacrylonitrile, bicomponent fibers and combinations thereof. The bicomponent fiber particles may be comprised of at least one of a polypropylene core with a polyethylene sheath, a polyester core with a polyethylene sheath, a polyester core with a polypropylene sheath, or a polyester core with a lower melting polyester sheath.

Partides may be fused to both opposing sides of the porous substrate. The barrier structure of this invention may also comprise more than one layer, either as separate layers unadheredly next to one another or as layers adhered to each other by bonding means such as heat, ultrasound, adhesive and combinations thereof. Additional layers may be of the type of which the barrier structure is comprised, wherein the sintered particles bearing side of one barrier structure layer may be either adjacent one side or the opposing side of its neighboring barrier structure layer. Purposes of such multiple layers are for example, to: provide additional resistance to liquid penetration, additional cushioning, comfort and dose fitting to the body. It is important, in a fluid resisting product, that the side of the barrier structure that has the sintered particles faces the fluid to which the product is to be a barrier. The additional layers may also be not of the type of which the barrier structure is comprised. Such additional layers may also or additionally comprise at least one additional porous substrate material, that is not a barrier structure, i.e., not having sintered particles fused to at least one side, such additional non-barrier substrates being either adjacent the one side, the opposing side or both sides of the porous layer. The uses of such additional layers are such as to provide additional absorbent capacity, cushioning, comfort and close fit to the body. Such additional layers may comprise for example at least one of a nonwoven fabric, woven fabric, perforated film or nonreticulated foam.

The barrier structures of this invention may be used to make absorbent products, by forming one or more components thereof, such as sanitary napkins, pantiliners, incontinence products, diapers, surgical dressings and bedding underpads. An example of such products will be given by describing in some detail a sanitary napkin. Such a sanitary napkin is generally rectangular, has opposing longitudinal edges and opposing transverse edges, and comprises a body facing liquid permeable sheet, an undergarment facing air permeable, liquid impermeable barrier, and an absorbent structure therebetween, the barrier being comprised of the barrier structure of this invention, and wherein the barrier structure has the sintered particles face the absorbent structure so that its fluid barrier properties are maximized. Such a sanitary napkin in use will permit air and water vapor to freely pass through and yet resist penetration of the barrier by body fluids such as urine, perspiration and menstrual fluid.

Body facing liquid permeable sheets may be comprised of at least a single layer or combinations of perforate film or foam or of a fabric such as is represented by wovens, knits and nonwovens, the nonwovens being represented by those such as are represented by the processes that produce spunbond, meltblown, needlepunched, thermobonded, chemical binder bonded, powder bonded, solvent bonded and hydroentangled fabrics. Perforate films may be such as those whose surfaces are flat or embossed, the bosses being of: micro size that may be visually detected as a matte finish or tactilely detected as having a silky, smooth feel; or of micro size where the individual bosses may be unaidedly seen or felt. The perforations may be two-dimensional, being essentially restricted to the plane of the film, or three-dimensional, wherein the film structure, that defines and supports the perforations, extends from the plane of the film and beyond, i.e., above or below, the plane of the film. Examples of combinations of the materials are those that may be formed by physical unadhered lamination, adhesive or thermal lamination or by interpenetrating lamination, e.g., fibrous webs laminated to the film in such fashion as to perforate the films. The foams may be reticulated and additionally perforated or nonreticulated and either additionally perforated or nonperforated. The surfaces of body facing layers, i.e., outer facing surface, or the surface which is the facing surface of the absorbent structure, may be: hydrophobic, hydrophilic, one surface may be hydrophobic and the other hydrophilic, or have gradients of hydrohobicity to hydrophilicity from one surface to the other.

The body facing liquid permeable sheet of the absorbent products of this invention may cover any part or all of the upper surface, that is the body facing surface, of the absorbent structure. It may alternatively wrap the absorbent structure partly or entirely around. Part wrapping of the absorbent structure is exemplified by the permeable body facing layer covering the top of and the sides of the absorbent structure. The body facing layer may be fixed or otherwise adhered to the surface of the absorbent structure overall or in discrete zones of attachment. Depending on the degree of coverage and wrapping of the absorbent structure by the body facing sheet, it may be adhered to itself for example in an overlapping configuration at the bottom of the absorbent structure. The garment facing barrier may cover at least the entire bottom surface, that is the garment facing surface, of the absorbent structure. It may also wrap around to cover the sides of the absorbent structure and even part of the body facing surface of the absorbent structure. The garment facing layer may be fixed or otherwise adhered to the surface of the absorbent structure overall or in discrete zones of attachment. The garment facing barrier may be adhered to the body facing sheet in an overlapping configuration for example parallel to the sides of the napkin or parallel to the bottom of the napkin or in a flange seal extending from the sides of the napkin. When the body facing sheet and garment facing barrier are adhered to each other in a flange seal, the body facing sheet may additionally be wrapped around the flange seal about the body facing sheet; or the garment facing barrier may additionally be wrapped around the flange seal about the body facing sheet.

Alternatively, the liquid permeable body facing cover sheet may be comprised of the barrier structure of this invention, yet being a liquid permeable sheet. Thus the liquid permeable body facing cover sheet is a perforate sheet having liquid permeable pores, but also having substantially liquid impermeable, but air permeable regions surrounding and between the liquid permeable pores, i.e., such regions forming the land areas between the liquid permeable pores. Examples of such perforate sheets and their methods of making are described above. In this application, the sintered particles of the substantially liquid impermeable regions may either face the absorbent structure of the napkin or may face the body of the user in use. Still alternatively, both the body facing liquid permeable sheet, as just described, and the undergarment facing air permeable, substantially liquid impermeable barrier may be comprised of the barrier structure of this invention.

The absorbent structure may be comprised either of simple or complex absorbent materials and structures that accept, transfer, distribute, store and retain fluid as well as prevent fluid from exiting the absorbent product. The absorbent structure may be a simple absorbent such as woodpulp, which may contain stabilizing components such as synthetic fibers, that are used as such, to form a bridging matrix; or by being thermobondable, are fused to themselves and to the woodpulp to form a dimension stabilizing structure. The synthetic fibers may be either hydrophilic, such as rayon, or hydrophobic such as polypropylene and polyester. The synthetic fibers may be made more wettable by treatment with a wetting agent such as a surfactant, by caustic etching of fibers such as polyester, by incorporating wettable polymers such as polyethylene oxide or polyvinyl alcohol within the fiber polymer formulation, by grafting the fiber surface with wettable reactants and by exposing the fiber to corona discharge.

The peripheral profile of synthetic fibers may be of any shape, e.g., round, oval, multilobal. The synthetic fibers may also contain grooves, channels or bores; and may be pitted or perforated. The absorbent structure may also contain auxiliary absorbents such as rayon or cotton fibers, sphagnum moss and superabsorbent fibers or particles.

Absorbents such as sphagnum moss, in board or in compressed layer form, may function additionally as compression resisting or deformation resisting structures or to help maintain one of a flat, concave or raised product profile, combinations thereof. Absorbents in board form may be made flexible and conforming by tenderizing means such as passing the board through a corrugating or embossing process. Woodpulp may also be comprised, at least in part, of any of wet crosslinked, dry crosslinked, chemically stiffened or curly fibers. The synthetic fibers and auxiliary absorbents may be present homogeneously throughout the absorbent structure, in discrete layers or in continuous or discontinuous concentration gradients. The absorbent structure may also contain foam in the form of layers or particles, the foam being either hydrophobic or hydrophilic, depending on its location and function in the product, e.g., absorbing, cushioning, deformation resisting and compression resisting. The absorbent structure may be uncompressed, compressed, or otherwise densified, at least in part. Compression and densification may be homogeneous throughout the absorbent structure or in discrete layers or in continuous or discontinuous gradients of density.

The absorbent structure may additionally comprise a transfer layer, which is a low density layer, that is fluid accepting and fluid releasing, and is usually located between a core body of the absorbent structure and the body facing sheet. The transfer layer may be comprised of relatively less hydrophilic materials and structures, than is contained in the absorbent core, such as of webs of meltblown polypropylene or polyester fibers. Such webs may also contain woodpulp entrained within. Transfer layers may also be comprised of low density, highloft nonwoven webs comprised of woodpulp and synthetic fibers such as polyethylene, polypropylene, polyester, polyacrylonitrile and polyamide. Such highloft webs may be bonded with chemical binders or by thermal means such as by through-air bonding.

Napkins of this invention may be provided with a means for attaching it to the undergarment such as adhesive, protected by release paper until use, or by mechanical attachments such as a hook and loop assembly, dasp assembly, hinge assembly or by combinations thereof. Release paper may be eliminated if the napkins of this invention are packaged in a wrapper that has a napkin facing surface that is of itself releasable from adhesive by virtue of being coated or formulated with a release substance such as silicone or fluorocarbon or by being physically altered, such as by embossing, to reduce its contact with the adhesive.

Napkins may be of many different shapes and sizes, depending on the requirements of the user with reference to her anatomy, menstrual flow volume and intensity, duration of wear and the part of the day or night the product is being worn. For example, napkins may be of generally rectangular shape, with generally straight or somewhat curved longitudinal and transverse edges, the corners defining the intersection of such edges being either square or rounded. Napkins may also be narrower in the central region than in the end regions, being of for example, of dogbone or hourglass shape; or they may be wider in the central region than in the end regions, being for example of oval or round shape. The end regions may or may not be symmetrical about the central region. The end regions may or may not be the same shape or size as each other.

The absorbent products of this invention may also comprise auxiliary components that may add to the functional, comfort and esthetic properties of the products. The products may include any or all of gasketing cuffs and garment attaching tabs, the tabs being also known as wings or flaps.

The tabs help maintain the surface of the central region of the napkin flat and spread open along the napkin's longitudinal axis. The tabs may emanate from the longitudinal edges of the napkin or they may be attached inwardly of the longitudinal edges of the absorbent structure of the napkin, the attachment of the latter tabs providing gathering of the crotch of the undergarment without diminishing the strike zone that is available to capture body fluids. The cuffs and tabs may be attached to or be extensions of the sanitary napkin of the napkin's body facing side, napkin sides or garment facing side. The cuffs and tabs may be comprised of materials that are different from those of the napkin, or may be comprised of materials of which the napkin is made, or of combinations of the different materials and the materials of which the napkin is made. When the cuffs and tabs are made of the materials of which the napkin is made, the materials may be attached to the napkin or be formed of extensions of the napkin's materials. Examples of constructions of cuffs and tabs are: where the permeable cover material and the impermeable barrier material are attached to themselves, or to each other, along the periphery of the cuff or tab structure, in discrete areas, or over their entire area of contact. The cuffs and tabs may have laminated, between the cover and barrier materials, extensions of part or all of the absorbent body, for example extensions of one or both of the transfer layer and a portion of the absorbent core. The tabs may be provided with adhesive, protected with release paper, for attachment to the undergarment, or they may be attached by mechanical attachments such as a hook and loop assembly, clasp assembly, hinge assembly or by combinations thereof. The cuffs and tabs may also contain additional materials to make them thick and cushioning and may also contain, separately or additionally, flexible, stretchable or elastic materials. Such materials have the effect, on the cuffs and tabs or wings, and at times on the napkin itself, of gathering, curving or causing to them to conform to the body and the garment. Embodiments of cuffs and tabs such as are described herein, and which are incorporated herein in their entirety are described in the following commonly assigned U.S. Pat. Nos. 4,940,462; 5,490,847 and 4,900,320.

As used throughout this application, the various abbreviations shall mean: in. (inch); ft (foot); mm (millimeter); cm (centimeter); m (meter); g (grams); min. (minute); and hr (hour).

The structure and function of this invention, including the barrier structure, and the products made therefrom, may be more clearly understood by referring to the following illustrative figures and test data. FIG. 1 is a plan view of a microphotograph 20, at 10×magnification, of the air permeable, substantially liquid impermeable barrier structure of this invention, showing a porous layer 2 having a porous substrate 4, here a polypropylene nonwoven that has been formed as a web by a spunbond process and then consolidated by embossing, here with square pattern embossments 6; and to which has been added fusible particles, here polyethylene, so that essentially even, uniformly spaced coverage of the surface of the nonwoven is achieved. The particle covered nonwoven was then transported to a heating means, such as an infrared oven, to fuse and sinter the particles to the substrate, and then brought through a nip between a chill roll and a rubber roll to yield flattened particles 8 that remain on the top of the nonwoven, but now have increased surface coverage and liquid repellency, to resist penetration of fluid in use through the porous fibrous nonwoven areas 10 on all sides of and beneath particles 8.

Figure 2:
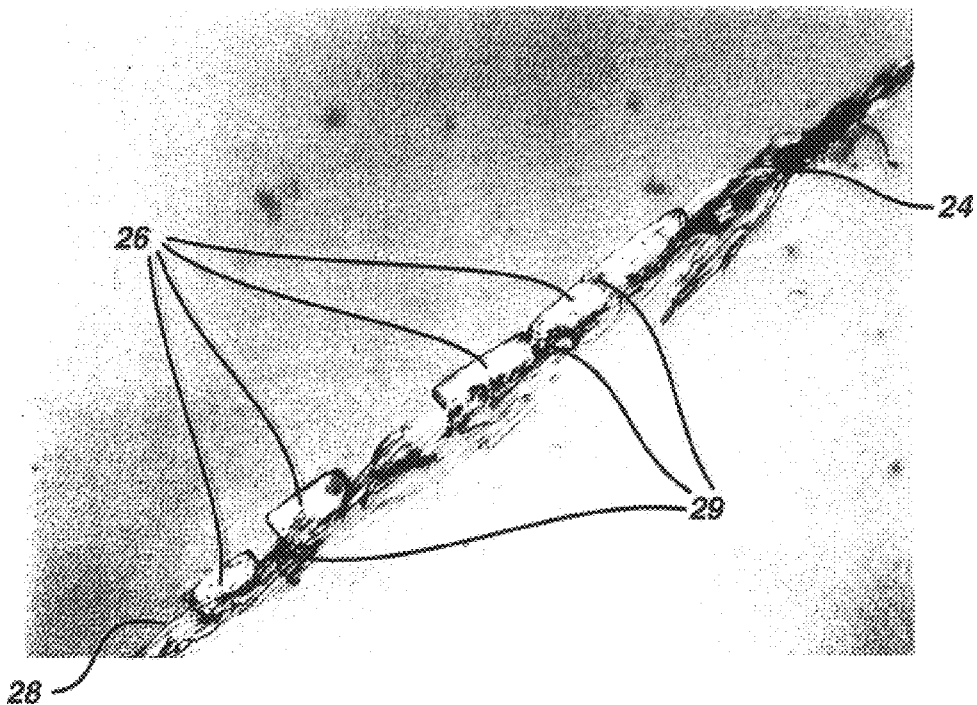
FIG. 2 is cross-section microphotograph of the air permeable, substantially liquid impermeable barrier structure of this invention, wherein particles have been adhered to a porous substrate by being sintered and then flattened.

FIG. 2 is cross section microphotograph 30, at 75×magnification, of air permeable, substantially liquid impermeable barrier structure porous layer 2 described in FIG. 1, having adhered, essentially to the surface 28, a spunbond fibrous polypropylene nonwoven porous substrate 24, flattened sintered particles 26 having sufficient coverage and liquid repellency to resist penetration of fluid in use through the porous fibrous nonwoven areas 29 on all sides of and beneath particles 26.

Figure 3:
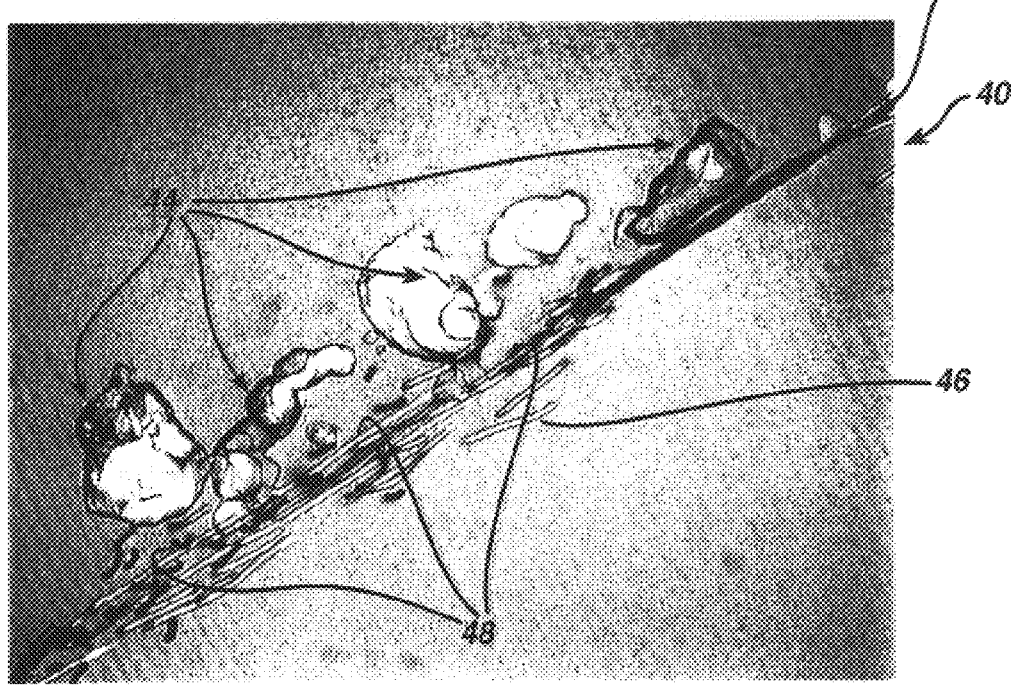
FIG. 3 is cross section microphotograph of an air permeable, substantially liquid impermeable barrier structure wherein particles have been adhered to a porous substrate by being sintered and not flattened.

FIG. 3, in contrast with FIG. 2, shows a cross section microphotograph 40, at 75×magnification, of a porous layer 42 having sintered particles 44 adhered to a spunbond fibrous polypropylene nonwoven porous substrate 46, wherein sintered particles 44 have not been brought through a nip between a chill roll and a rubber roll to yield flattened particles give optimum resistance to penetration by fluid in use through the porous fibrous nonwoven areas 48 of porous substrate 46.

Figure 4:
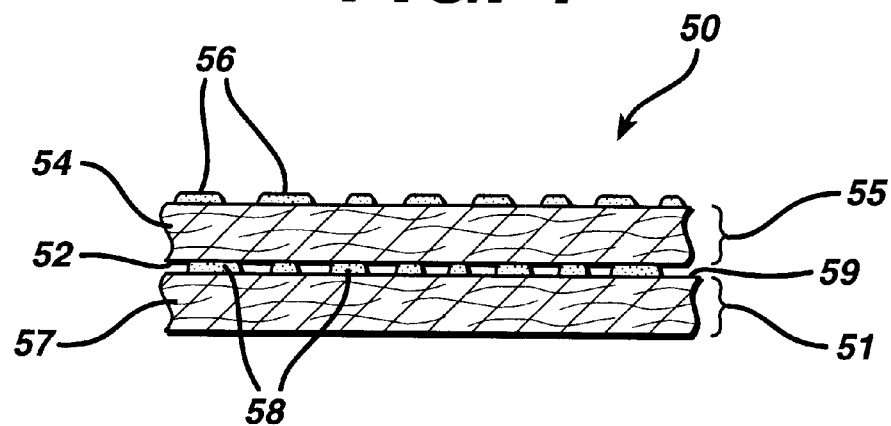
FIG. 4 is a cross section view of the barrier structure of this invention having an additional porous layer of this invention adjacent one side of the barrier structure of this invention.

FIG. 4 is a cross sectional view 50 of a barrier structure of this invention 50 having an additional porous layer 51 of this invention adjacent one side 52 of a barrier structure 55 of this invention, barrier structure 55 having a porous substrate 54 that has adhered to it sintered, flattened particles 56. Additional porous layer 51, as shown herein, is also comprised of the barrier structure of this invention, here having sintered flattened parties 58 adhered to one side 59 of porous substrate 57. Additional porous layer 51 may be comprised of any porous material 57 such as a wood pulp pad, nonwoven, woven, perforate film and non reticulated foam; and may optionally have sintered flattened particles adhered to it.

Figure 5:
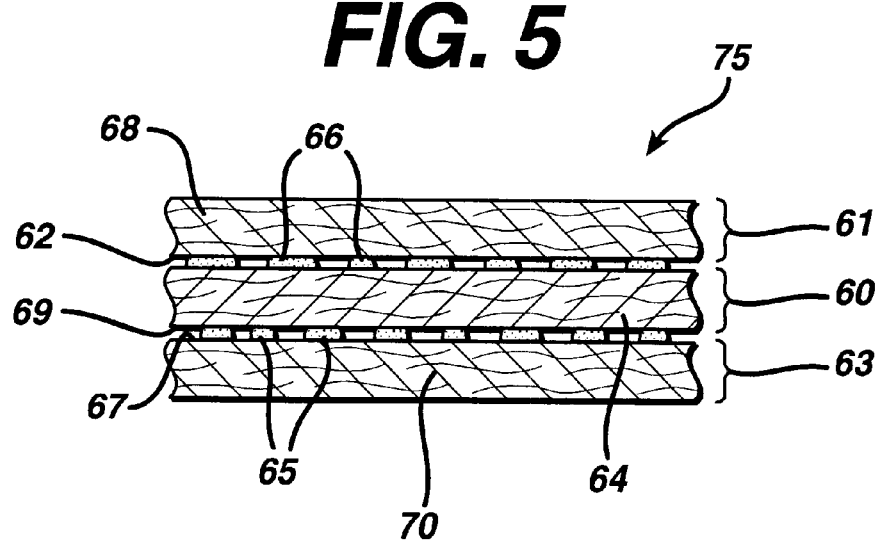
FIG. 5 is a cross section view of the barrier structure of this invention having two additional porous layers of this invention, one adjacent one side of the barrier structure of this invention and the other adjacent the other side of the barrier structure of this invention.

FIG. 5 is a cross sectional view 75 of a barrier structure 60 of this invention having two additional porous layers 61, 63. Additional porous layer 61 is adjacent one side 62 of barrier structure 60 that is comprised of a porous substrate 64 that has adhered to it sintered, flattened particles 66. Porous layer 63 is adjacent the opposite side 69 of barrier structure 60. Additional porous layers 61, 63 may or may not be comprised of the barrier structure of this invention. Additional porous layer 61, as shown herein, is comprised of a porous material 68. Additional porous layer 63, as shown herein, is comprised of a barrier structure of this invention having sintered flattened particles 65 adhered to one side 67 of a porous substrate 70. Additional porous layers 61, 63 may or may not be the same as each other in terms of structure, material composition and weight.

Figure 6:
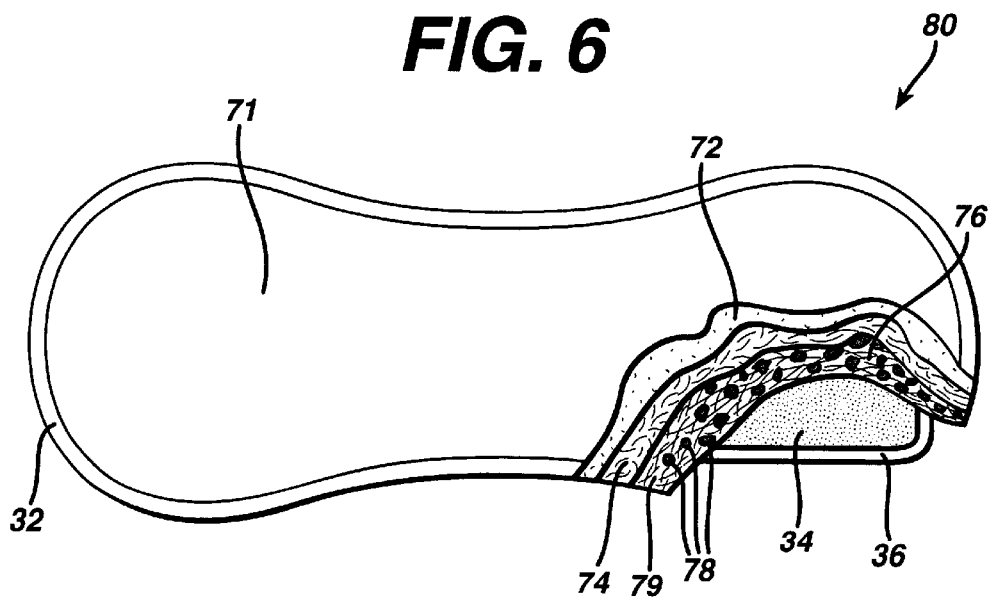
FIG. 6 is a partially broken perspective view of a sanitary napkin of this invention having an undergarment facing air permeable, substantially liquid impermeable barrier structure of this invention.
Figure 7:
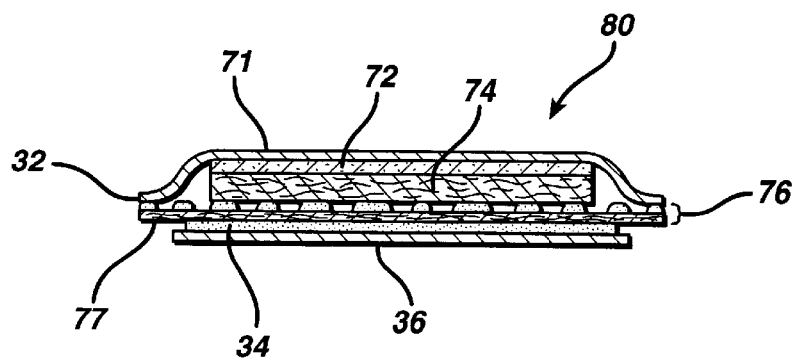
FIG. 7 is a cross section view of the sanitary napkin shown in FIG. 6.

The following discussion refers to both FIGS. 6 and 7. FIG. 6 is a partially broken perspective view of a sanitary napkin 80 of this invention having sequentially a permeable cover sheet 71, optionally a liquid transfer layer 72, a liquid absorbing and retaining absorbent core 74 and an undergarment facing air permeable, substantially liquid permeable barrier structure 76 of this invention, the sintered flattened particles 78 of barrier structure 76 being adhered preferably to the surface 79 that is adjacent absorbent core 74. Absorbent core 74 may optionally contained hydrophilic components such as woodpulp, rayon and cotton and thermoplastic fibers such as polyethylene, polypropylene, polyester and polyamide, such fibers being optionally treated to be hydrophilic by means such as surfactants, wetting agents and chemical and radiation induced grafting and surface modification and by corona discharge. Absorbents may optionally contain highly absorbent species such as: preferably non-gelblocking superabsorbents; curly fibers; channeled fibers containing channels internal to the fiber surface or external to the fiber surface. Napkin 80 may optionally contain other liquid transport guidance means such as layers of tissue, internal and external embossed patterns and external and internal embossed channels. Transfer layer 72 and absorbent core 74 may comprise gradients of materials in decreasing or increasing concentrations and increasing or decreasing densities, such gradients being located laterally or vertically throughout or in at least a portion of transfer layer 72 and absorbent core 74. Cover sheet 71 and barrier structure 76 may be sealed to one another in a flange seal 32, as shown herein, or wrapped about each other overlappingly and optionally sealed to each other, for example: cover sheet 71 wrapped about barrier structure 76 or barrier structure 76 wrapped about cover sheet 71. Garment facing outer surface 77 of barrier structure 76 may have a positioning adhesive 34 for attaching napkin 80 to an undergarment, adhesive 34 being optionally protected by a release surface material 36, for example siliconized release paper, that is removed prior to use. Napkin 80 may optionally be attached to the garment by mechanical means such as hook and loop attachments, by frictional materials or by snaps or clips.

FIG. 7 is a cross section view of the sanitary napkin 80 shown in FIG. 6, the components of napkin 80 having the same designating numerals.

Figure 8:
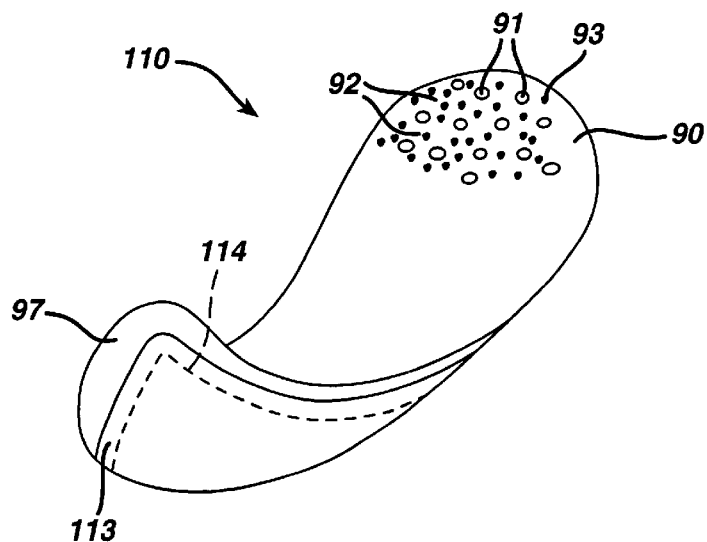
FIG. 8 is a perspective view of a sanitary napkin of this invention having a body facing liquid permeable cover sheet comprised of liquid permeable pores and liquid impermeable, but air permeable regions, where such regions comprise the air permeable, substantially liquid impermeable barrier structure of this invention.
Figure 9:
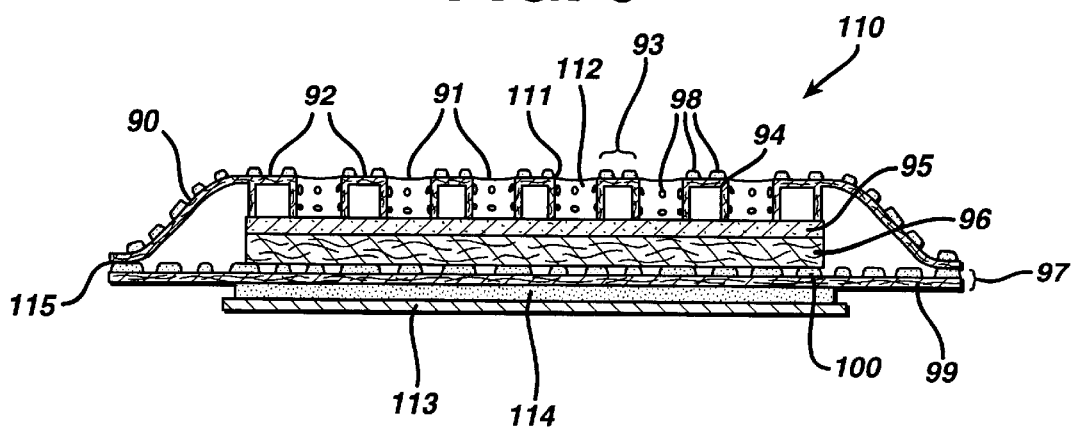
FIG. 9 is a cross section view of the sanitary napkin shown in FIG. 8.

The following immediate discussion refers to both FIGS. 8 and 9. FIG. 8 is a perspective view of a sanitary napkin 110 of this invention having a body facing liquid permeable cover sheet 90 comprised of liquid permeable pores 91 and substantially liquid impermeable, but air permeable regions 92, where such regions comprise the air permeable, substantially liquid impermeable barrier structure 93 of this invention, where regions 92 are comprised of a porous substrate 94 to which are adhered sintered flattened particles 98. Napkin 110 has, sequentially, permeable cover sheet 90, optionally a liquid transfer layer 95, a liquid absorbing and retaining absorbent core 96 and an undergarment facing air permeable, liquid permeable barrier structure 97 of this invention, where barrier structure 97 comprises a nonwoven substrate 99 to which are adhered sintered flattened particles 100, where particles 100 of barrier 97 are preferably adjacent absorbent core 96. Sintered flattened particles 98 of liquid permeable cover sheet 90, as shown in FIGS. 8 and 9, are on the body facing side 111 of substantially liquid impermeable, but air permeable regions 99, and also line the body facing surface 112 of liquid permeable pores 91, such pores being of sufficient diameter to permit the transfer of liquid. However sintered flattened particles 98 may also and optionally be located on the side of cover sheet 90, thereby facing transfer layer 95. Cover sheet 90 and barrier structure 97 are herein sealed to one another in a flange seal 115. Undergarment facing barrier structure 97 may have a positioning adhesive 114 for attaching sanitary napkin 110 to an undergarment, adhesive 114 being optionally protected by a release surface material 113 that is removed prior to use.

FIG. 9 is a cross section view of the sanitary napkin shown in FIG. 8, the components of napkin 110 having the same designating numerals.

EXAMPLES

Table 1 gives the air permeability and resistance to leakage of the macroporous barrier structure of this invention, alone and combination with an absorbent product, as well as for microporous films on such and absorbent product. The weight of the spunbond and the and-on of the sintered particles are given in grams per square meter (noted as gsm).

1. Measurement of Air Permeability of Nonocclusive Materials

Air permeability is the volume rate of airflow passing through a square foot sample of material, in cubic feet per minute, that is necessary to maintain an air pressure across the sample of 0.5 inch (1.25 cm) of water. The Frazier Air Permeometer (Frazier Precision Instrument Company, Inc., Hagerstown, Md.) indirectly determines this airflow by measuring the pressure drop across the sample in the test chamber through which the air is passing. A calibration curve is used to convert the pressure drop readings to air permeability. A sample is clamped in place at the entrance to a first chamber which communicates through an orifice to a second chamber wherein the air flow differential is created by means of a suction fan, the size of the orifice being appropriate to the anticipated air permeability range to be measured. The suction is increased to the point where the pressure in the first chamber as recorded on an inclined oil manometer is 0.5 inch (1.25 cm) of water. The pressure in the second chamber as recorded on a vertical oil manometer and is converted to air permeability by means of a conversion chart.

2. Measurement of Resistance to Leakage of Permeable Materials

A stack of four 4×8 in. (10.2×20.3 cm) sheets of Whatman No. 1 Qualitative filter paper is weighed. The test sample comprising a test absorbent product is placed with its barrier structure downward in contact with the top sheet of the filter paper stack. The test absorbent product herein was a 2.5 ounces per square yard (about 85 g/m$^2$) material comprised of about 45% woodpulp and 55% fusible fiber, the fusible fiber being of the bicomponent type, having a fusible lower melting outer sheath surrounding a higher melting core. A Plexiglas® acrylic plate, 2 inches wide (about 5 cm), 8 inches (about 20 cm) long and 7/16 inches (about 1 cm) thick and containing an orifice 0.5 inch (about 1.25 cm), for admitting fluid is placed on top of the absorbent structure. Two 2 kilogram weights are placed on either side of the orifice and 1.3 milliliters red dyed 0.9% saline solution is poured through the orifice at an even rate. One minute after the fluid has been completely added the filter paper is weighed to determine how much fluid, if any, has leaked through the barrier structure, and the stain area, if any, is measured.

TABLE 1

Air Permeability and Resistance to Leakage of the Macroporous Barrier Structure of this Invention and Microporous Films, Alone and Combination with an Absorbent product

| Barrier Structures Area | Frazier Air Permeability mm$^3$/ft$^2$/min (mm$^3$/m$^2$/min) | Leakage g/product | Stain in$^2$ (cm$^2$) |
|---|---|---|---|
| Spunbond, 19 gsm | >700 (>7525) | | |
| Spunbond, 19 gsm on Absorbent Product | 45 (483.75) | 0.01 | 0.2 (1.3) |
| Spunbond, 19 gsm with 17.9 gsm sintered particles (~300 microns diameter) | >700 (>7525) | | |
| Spunbond, 19 gsm with 17.9 gsm sintered particles ~300 microns diameter on Absorbent Product | 48 (516) | 0 | 0 |
| Exxon BF100W Microporous Film | 0 | | |
| Exxon BF100W Microporous Film on Absorbent Product | 0 | 0 | 0 |

We claim:

1. An absorbent product, having opposing longitudinal edges and opposing transverse edges, and comprising a body facing liquid permeable sheet, an undergarment facing air permeable, substantially liquid impermeable barrier structure, and an absorbent structure therebetween, the barrier structure comprising at least one porous layer having opposing sides, the porous layer being comprised of:

a porous substrate having pores, which extend between opposing sides that correspond to the opposing sides of the porous layer, whereby a liquid may transverse the substrate; and particles that are fused to the at least one side of the porous substrate so as to restrict entry of the liquid into the pores;

wherein the porous layer substantially resists penetration by the liquid when it is contained in a test absorbent product that overlays the first side of the porous layer to which the particles are fused, and is under a loading of one pound per square inch; and wherein the barrier structure has a Frazier air permeability value of greater than zero $mm^3/m^2/min$.

2. The absorbent product of claim 1 wherein the porous substrate is selected from the group consisting of perforated film, nonwoven fabric, nonreticulated foam and combinations thereof.

3. The absorbent product of claim 2 wherein the nonwoven fabric has a basis weight of at least about 8 grams per square meter.

4. The absorbent product of claim 2 wherein the nonwoven fabric is made from thermoplastic staple fibers, thermoplastic filaments, nonthermoplastic staple fibers or nonthermoplastic filaments.

5. The absorbent product of claim 4 wherein the thermoplastic staple fibers and thermoplastic filaments are selected from the group consisting of polyethylene, polypropylene, polyester, polyamide, polacrylonitrile, bicomponent fibers and combinations thereof.

6. The absorbent product of claim 5 wherein the bicomponent fibers are comprised of at least one of a polypropylene core with a polyethylene sheath, a polyester core with a polyethylene sheath, a polyester core with a polypropylene sheath, or a polyester core with a lower melting polyester sheath.

7. The absorbent product of claim 4 wherein the fibers and filaments are bonded to each other by thermal calender bonding, fusible powder bonding; adhesive binder bonding; spunbonding; or meltblowing followed by calender bonding or hydroentangling.

8. The absorbent product of claim 4 wherein the nonthermoplastic fibers are selected from the group consisting of cotton, rayon, woodpulp and combinations thereof.

9. The absorbent product of claim 1 wherein the absorbent product is a sanitary napkin or an incontinence product.

10. The absorbent product of claim 1 wherein the absorbent structure is comprised of a transfer layer or an absorbent core.

11. The absorbent product of claim 1 further having at least one wing for wrapping the absorbent product about the undergarment, the wing being attached to one longitudinal edge of the absorbent product.

12. The absorbent product of claim 1 further having at least one wing attached to the porous sheet inwardly of one longitudinal edge of the absorbent product.

13. The absorbent product of claim 1 wherein the porous substrate further comprises a nonwoven fabric, a woven fabric, a perforated film or a nonreticulated foam.

14. The absorbent product of claim 1 wherein the test absorbent product is a sanitary napkin.

15. The absorbent product of claim 1 wherein the side of the porous sheet to which the particles are fused is adjacent the absorbent structure.

16. The absorbent product of claim 1 wherein the particles are present in an amount of at least about 9 grams per square meter.

17. The absorbent product of claim 16 wherein the particles are present in an amount of from about 9 to about 36 grams per square meter.

18. The absorbent product of claim 1 which further comprises at least one additional porous layer adjacent the first side of the porous layer.

19. The absorbent product of claim 1 wherein the porous layer has a Frazier air permeability value in the range of from about 5 $mm^3/ft^2/min$ to about 70 $mm^3/ft^2/min$.

20. The absorbent product of claim 1 wherein the porous layer has a Frazier air permeability value in the range of from about 25 $mm^3/ft^2/min$ to about 60 $mm^3/ft^2/min$.

21. The absorbent product of claim 1 wherein the particles are selected from the group consisting of polyethylene, polypropylene, polyester, ethylenevinyl acetate, ethylene acrylic acid, ethylene methacrylate, ethylene n-butylacrylate, polyester polyurethanes, polyether polyurethanes, styrene-isoprene-styrene copolymers, styrene-butadiene-styrene copolymers, styrene-ethylene-butylene-styrene copolymers, styrene-ethylene-propylene-styrene copolymers and combinations thereof.

22. The absorbent product of claim 1 wherein the particles are selected from the group consisting of polyethylene, polypropylene, polyester, polyamide, polacrylonitrile, bicomponent fibers and combinations thereof.

* * * * *